US012539190B2

(12) United States Patent
Brown

(10) Patent No.: US 12,539,190 B2
(45) Date of Patent: Feb. 3, 2026

(54) SHIELD N.GUIDE

(71) Applicant: Calvette Brown, Riverside, IL (US)

(72) Inventor: Calvette Brown, Riverside, IL (US)

( * ) Notice: Subject to any disclaimer, the term of this patent is extended or adjusted under 35 U.S.C. 154(b) by 808 days.

(21) Appl. No.: 16/877,486

(22) Filed: May 19, 2020

(65) Prior Publication Data

US 2021/0361374 A1 Nov. 25, 2021

(51) Int. Cl.
*A61B 90/00* (2016.01)
*A61H 3/00* (2006.01)

(52) U.S. Cl.
CPC ................ *A61B 90/05* (2016.02); *A61H 3/00* (2013.01); *A61H 2201/0192* (2013.01); *A61H 2201/1635* (2013.01)

(58) Field of Classification Search
CPC ........... F41H 5/08; A63B 69/26; A63B 69/28; A63B 69/004; A61G 7/10; A61G 7/1053; A61G 7/1023; A61G 7/1013; A61G 7/1038
See application file for complete search history.

(56) References Cited

U.S. PATENT DOCUMENTS

| | | | | | |
|---|---|---|---|---|---|
| 1,279,571 | A * | 9/1918 | Moloney | F41H 5/08 | 2/2.5 |
| 1,612,945 | A | 1/1927 | Rieck | | |
| 2,477,989 | A * | 8/1949 | La Maida | F41H 5/08 | D29/101.1 |
| 3,248,852 | A | 5/1966 | Schwartz | | |
| 4,577,591 | A | 3/1986 | Wesseldine | | |
| 5,467,743 | A | 11/1995 | Doose | | |
| 5,632,235 | A | 5/1997 | Larsen et al. | | |
| 5,641,934 | A * | 6/1997 | Follett | F41H 5/0407 | 89/36.05 |
| 5,674,159 | A * | 10/1997 | Davidson | A63B 21/1663 | 482/904 |
| 5,970,921 | A | 10/1999 | Fulton | | |
| 6,481,383 | B1 | 11/2002 | Ross et al. | | |
| 7,370,608 | B1 | 5/2008 | Friedman | | |
| 8,408,730 | B2 | 4/2013 | Hurwitz | | |
| 8,424,495 | B2 | 4/2013 | Rivera-Brutto | | |
| 8,807,090 | B1 | 8/2014 | Potts et al. | | |

(Continued)

FOREIGN PATENT DOCUMENTS

WO 2017184653 A1 10/2017

*Primary Examiner* — Samuel G Gilbert
(74) *Attorney, Agent, or Firm* — Faegre Drinker Biddle & Reath LLP

(57) ABSTRACT

A wearable device for human guides (hereafter referred to as "the guide") and persons in need of person to person contact assistance (herein referred to as "the guide"). Preferably for use within, but not limited to, medical, educational and retail institutions for the disabled and seniors in need of travel assistance from point a to point b. The present invention relates to an apparatus which is worn over the shoulder or across the backside by a person who is a guide and has a handle for grasping by another person who needs to be guided and is connected to a shield betwixt the two devices to serve as a barrier between the two said person there by protecting both parties from cross contamination and body fluids. A device used to deter direct human to human contact and to promote safety and social distancing while traveling in close proximity of one another.

3 Claims, 5 Drawing Sheets

(56) References Cited

U.S. PATENT DOCUMENTS

| | | | | |
|---|---|---|---|---|
| 9,022,904 | B1 * | 5/2015 | Dorsey, III ............ | A63B 69/26 482/88 |
| 9,332,734 | B1 | 5/2016 | Hege | |
| 9,339,015 | B2 | 5/2016 | Pinto | |
| 2005/0072376 | A1 | 4/2005 | Kerrigan | |
| 2006/0043135 | A1 * | 3/2006 | Lindsey ................. | A45C 3/001 224/576 |
| 2006/0090711 | A1 | 5/2006 | Richards | |
| 2006/0278177 | A1 | 12/2006 | Crawford | |
| 2007/0272170 | A1 | 11/2007 | Milson et al. | |
| 2010/0043725 | A1 | 2/2010 | Hall | |
| 2010/0269765 | A1 | 10/2010 | Barghahn | |
| 2010/0313825 | A1 | 12/2010 | Friedland | |
| 2011/0174237 | A1 | 7/2011 | Sanders-Luckman et al. | |
| 2011/0277703 | A1 | 11/2011 | Yeaw | |
| 2011/0297107 | A1 | 12/2011 | Kostelec | |
| 2012/0180635 | A1 * | 7/2012 | Garcia ...................... | F41H 5/08 89/926 |
| 2013/0014705 | A1 | 1/2013 | Cho et al. | |
| 2013/0276719 | A1 | 10/2013 | Ferrando | |
| 2014/0024503 | A1 * | 1/2014 | Chiang .................. | A63B 69/26 482/83 |
| 2014/0190424 | A1 | 7/2014 | Howell | |
| 2014/0355256 | A1 | 12/2014 | Curtis | |
| 2015/0245897 | A1 | 9/2015 | Hasebi et al. | |
| 2016/0095417 | A1 * | 4/2016 | Bruffey ..................... | A45F 3/04 224/645 |
| 2017/0136335 | A1 * | 5/2017 | Bentley .................. | A63B 69/26 |
| 2017/0156295 | A1 | 6/2017 | Zoltanski | |

* cited by examiner

SHIELD N.GUIDE

BACKGROUND

Persons in need of walking assistance from a human guide, such as but not limited to the disabled and senior people, can be guided comfortably and safely by outfitting the guiding person with a shied attached to a handle for throwing shield over the shoulder or back on the front end by the guide and an inverted or outward handle to be grasped by the guide on the opposite side of the shield and is molded or mounted onto a shield of varying shapes, sizes, textures and colors, opaque or transparent for protection from cross-contamination by both persons.

One drawback to current guide processes, in particular, the healthcare industry for seniors and the disabled is that there is no room to allow for personal space or protection from bodily fluids and contaminants when guides assist guides. Also, although human guides are used to being touched (sometime inappropriately the "classic" method), which allows for direct person to person contact, it is no longer a safe method. A need exists for a space shield that can be readily thrown over the working guides shoulder while simultaneously allowing a person in need of travel assistance to grab a handle that is connected to the outer opposite end of the shield. The shield is for travel safety, personal space for both guide and guide, and sanitation while transporting another person to points of destinations.

SUMMARY

A shield having inverted and/or outward collapsible handles and/or straps affixed to the shield which are but not limited to being detachable or folding on both sides of the shield, such that, when the shield is to be placed over the shoulder by person A (the guider) as a no-contact barrier and grasping device for purposes of guiding person B (the needing travel assistance) to the destination point while avoiding bodily contact and allowing for social distancing in the process. This unit is not limited to but is preferably used while assisting the elderly or disabled while being guided to the destination point.

In a first aspect of the invention, a combination of a plastic shield which attaches to two handles extended from both sides of the shield comprises a shield having but not limited to the plurality of molded inverted or outward handles or straps of various materials, sizes, shapes, colors and adhesions: a first handle affixed to the shields front panel for the purpose of throwing or mounting over guides shoulder; and a second set of handles or straps, affixed to the shield back panel; such that, when the harness is placed around the body part, preferably but not limited to the shoulder or across the backside of the guiding person. The handles can be molded to each other through the shield. A combination harness strap and attachable shield comprises but are not limited to material of clear simple plastic, fiberglass, or plexi-glass rigid and/or flexible for the guiding person's head and/or body; and or more fasteners affixed thereto, with at least one fastener being affixed to the harness and at least one counterpart fastener being affixed to the shield. The shield is attached to or molded into the harness by engaging corresponding mating fasteners with one another.

BRIEF DESCRIPTION OF THE FIGURES

Various features and advantages of the invention will be understood more completely when considered in connection with the accompanying drawings (which are not necessarily drawn to scale; wherein:

FIG. 3A depicts the front perspective view of the shield. FIG. 3B depicts the back perspective view of a shield.

DETAILED DESCRIPTION

Figure 1A:
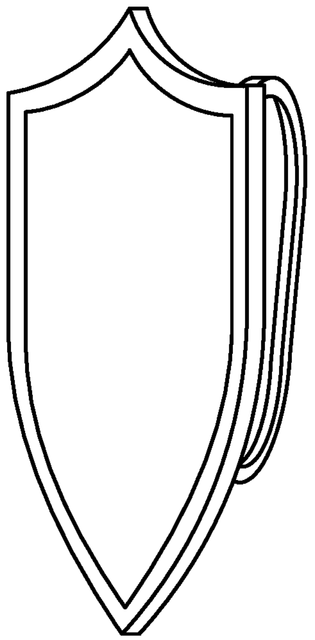
FIG. 1A depicts a front perspective view of a shield according to a first embodiment with an attached handle.
Figure 1B:
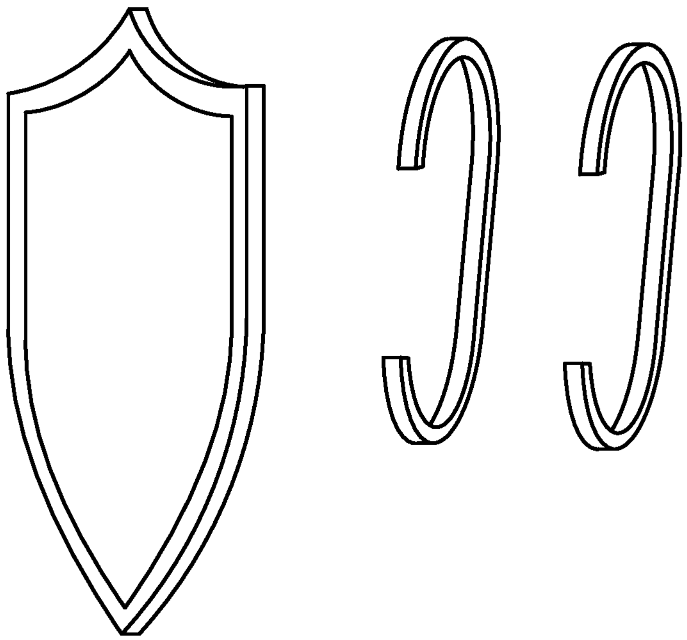
FIG. 1B depicts a front perspective view of the shield of FIG. 1A with the handle detached.
Figure 2A:
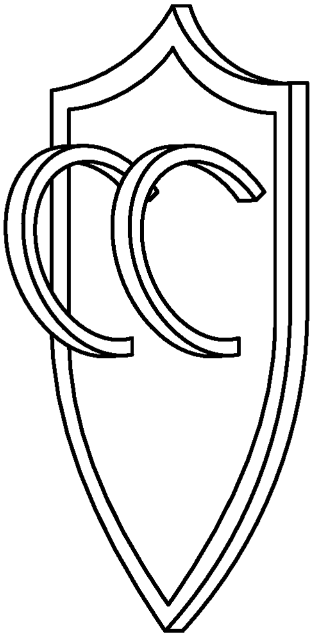
FIG. 2A depicts a back perspective view of a shield according to a second embodiment with an attached handle.
Figure 2B:
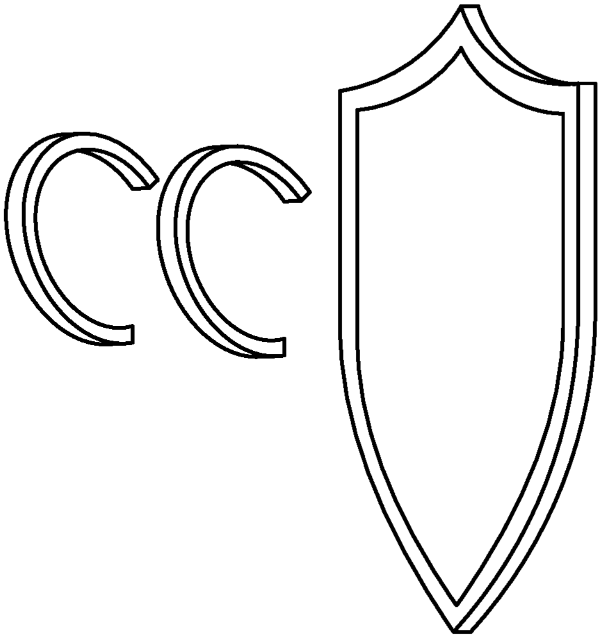
FIG. 2B depicts a back perspective view of the shield of FIG. 2A with the handle detached.
Figure 2C:
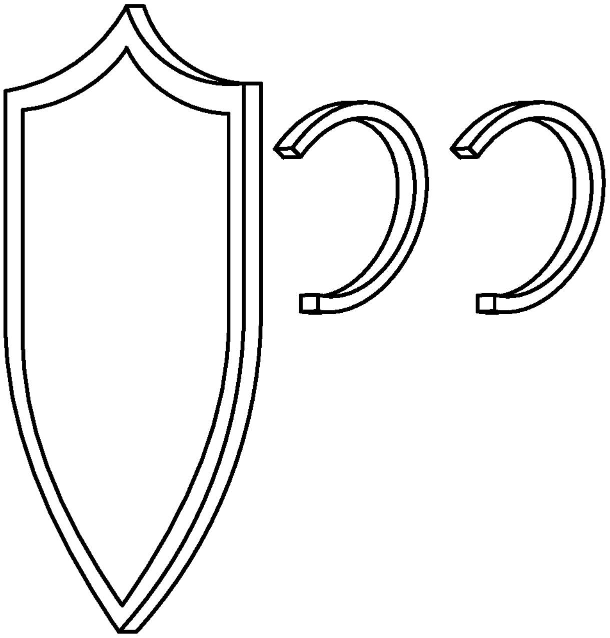
FIG. 2C depicts a back perspective view of the shield of FIG. 2A with the handle detached from an inverted handle position.
Figure 3A:
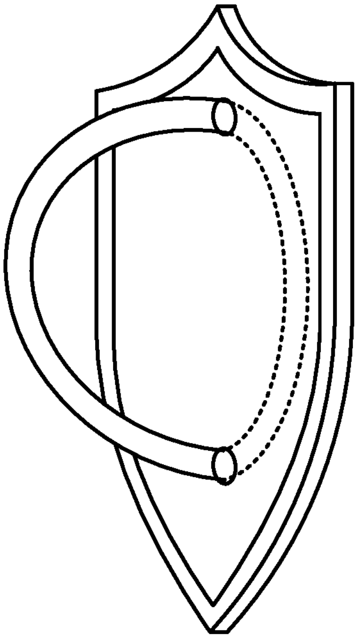
FIGS. 3A and 3B depict a shield according to a third embodiment, wherein one strap slides through the shield. That is, the strap slides through the shield so that the same strap acts as a handle for both sides of the shield.
Figure 3B:
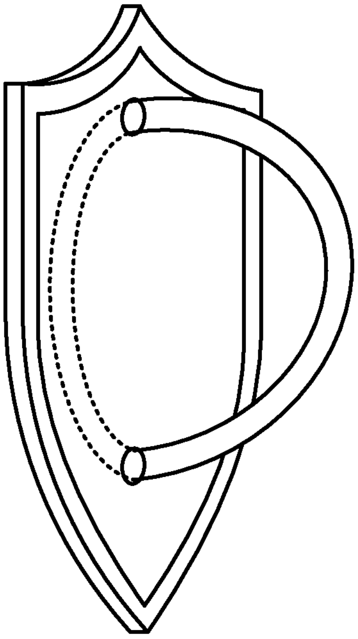

In one embodiment, the invention is a shield worn over the shoulder of a person thereby having a strap of various material used as a holding mechanism to be held by the person being guided and an attachable shield is depicted. The combination includes a shield, having a shoulder strap or handle. The entire unit preferably but not limited to being rigid; and an attachable grasping handle. The shield has a number of intrinsic properties and purposes, such as protective barriers, decoration, various sizes and shapes etc., and is constructed of a material or materials amenable to such purpose(s). Unlimited examples include natural and synthetic fabrics, plastic handles, or soft, plastic, mesh, composites, shapes, sizes and the like.

Upon reading this disclosure, other embodiments and modifications will be apparent to the skilled person. For example, the handles and straps can be affixed to the shield, in a manner other than as described. These optional fasteners enable the shield and handles to be worn over shoulder or across the backside and thereby secure the shield to the arm or backside of the guiding person. All such embodiments and modification fall within the scope of the present invention, which is limited only by the appended claims and equivalents thereof.

REFERENCES CITED

| U.S. PATENT DOCUMENTS: | | |
|---|---|---|
| 1,612,945 | January 1927 | Rieck |
| 3,248,852 | May 1966 | Schwartz |
| 4,577,591 | March 1986 | Wesseldine |
| 5,467,743 | November 1995 | Doose |
| 5,632,235 | May 1997 | Larsen |
| 5,970,921 | October 1999 | Fulton |
| 6,481,383 | November 2002 | Ross |
| 7,370,608 | May 2008 | Friedman |

-continued

| | | |
|---|---|---|
| 84U873U | April 2013 | Hurwitz |
| 8,424,495 | April 2013 | Rivera-Brutto |
| 8,807,090 | August 2014 | Potts |
| 9,332,734 | May 2016 | Hege |
| 9,339,015 | May 2016 | Pinto |
| 2005/0072376 | April 2005 | Kerrigan |
| 2006/0090711 | May 2006 | Richards |
| 2006/0278177 | December 2006 | Crawford |
| 2007/0272170 | November 2007 | Milson et al. |
| 2010/0043725 | February 2010 | Hall |
| 2010/0269765 | October 2010 | Barghaln |
| 2010/0313825 | December 2010 | Friedland |
| 2011/0174237 | July 2011 | Sanders-Luckman |
| 2011/0277703 | November 2011 | Yeaw |
| 2011/0297107 | December 2011 | Kostelec |
| 2013/0014705 | January 2013 | Cho |
| 2013/0276719 | October 2013 | Ferrando |
| 2014/0190424 | July 2014 | Howell |
| 2014/10355256 | December 2014 | Curtis |
| 2015/0245897 | September 2015 | Hasebi |
| 2017/0156295 | June 2017 | Zoltanski |

FOREIGN PATENT DOCUMENTS

| | | |
|---|---|---|
| WO/2017184653 | October 2017 | CALDERA INTERNATIONAL, INC. |

What is claimed is:

1. A protective shield comprising:

a barrier having a first major surface and a second major surface and configured to block contact between a guider and a person being guided;

a first pair of handles attached to and in direct contact with the first major surface and configured to be placed over a shoulder of the guider; and a second pair of handles attached to and in direct contact with the second major surface and configured to be grasped by the person who is being guided, wherein the barrier is formed of plexiglass.

2. The protective shield of claim 1, wherein the first pair of handles or the second pair of handles is detachable from the barrier.

3. The protective shield of claim 1, wherein the second pair of handles are inverted.

* * * * *